(12) United States Patent
Bogue

(10) Patent No.: US 9,095,495 B2
(45) Date of Patent: Aug. 4, 2015

(54) DEVICE AND SYSTEM FOR DETERMINING, PREPARING AND ADMINISTERING THERAPEUTICALLY EFFECTIVE DOSES

(75) Inventor: Beuford A. Bogue, New Carlisle, IN (US)

(73) Assignee: MONOSOL RX, LLC, Warren, NJ (US)

( * ) Notice: Subject to any disclaimer, the term of this patent is extended or adjusted under 35 U.S.C. 154(b) by 663 days.

(21) Appl. No.: 12/711,899

(22) Filed: Feb. 24, 2010

(65) Prior Publication Data

US 2011/0208348 A1    Aug. 25, 2011

(51) Int. Cl.

| | |
|---|---|
| *G06F 17/00* | (2006.01) |
| *A61B 5/00* | (2006.01) |
| *B65D 83/00* | (2006.01) |
| *B65D 83/08* | (2006.01) |
| *A61J 7/00* | (2006.01) |
| *G06F 19/00* | (2011.01) |

(52) U.S. Cl.
CPC ............. *A61J 7/0076* (2013.01); *A61B 5/0095* (2013.01); *G06F 19/3462* (2013.01); *A61J 7/0084* (2013.01)

(58) Field of Classification Search
CPC ............................ A61J 7/0076; A61J 7/0084
USPC .................................................. 700/237, 240
See application file for complete search history.

(56) References Cited

U.S. PATENT DOCUMENTS

| | | | | |
|---|---|---|---|---|
| 4,712,460 A | * | 12/1987 | Allen et al. | 83/208 |
| 5,036,462 A | * | 7/1991 | Kaufman et al. | 600/300 |
| 5,084,828 A | * | 1/1992 | Kaufman et al. | 700/242 |
| 5,102,008 A | * | 4/1992 | Kaufman et al. | 221/25 |
| 5,119,969 A | * | 6/1992 | Haber | 221/71 |
| 5,126,957 A | * | 6/1992 | Kaufman et al. | 700/242 |
| 5,142,484 A | * | 8/1992 | Kaufman et al. | 222/638 |
| 5,148,944 A | * | 9/1992 | Kaufman et al. | 221/131 |
| 5,197,632 A | * | 3/1993 | Kaufman et al. | 221/197 |
| 5,230,441 A | * | 7/1993 | Kaufman et al. | 221/25 |
| 5,267,174 A | * | 11/1993 | Kaufman et al. | 700/242 |
| 5,335,816 A | * | 8/1994 | Kaufman et al. | 221/13 |
| 5,820,877 A | | 10/1998 | Yamaguchi et al. | |
| 5,945,651 A | * | 8/1999 | Chorosinski et al. | 235/375 |
| 6,304,797 B1 | * | 10/2001 | Shusterman | 700/243 |
| 6,394,306 B1 | | 5/2002 | Pawlo et al. | |
| 6,601,729 B1 | * | 8/2003 | Papp | 221/25 |
| 6,962,266 B2 | * | 11/2005 | Morgan et al. | 221/25 |
| 7,040,503 B2 | * | 5/2006 | Leichter et al. | 221/73 |
| 7,264,136 B2 | * | 9/2007 | Willoughby et al. | 221/3 |

(Continued)

OTHER PUBLICATIONS

Notification of Transmittal of the International Search Report and the Written Opinion of the International Searching Authority, or the Declaration for International Application No. PCT/US11/25804 dated Apr. 11, 2011.

(Continued)

*Primary Examiner* — Michael K Collins
(74) *Attorney, Agent, or Firm* — Hoffmann & Baron, LLP

(57) ABSTRACT

The present invention relates to a system and method for dispensing a therapeutically effective amount of dosage containing a medicament including an instrument for inputting data from a user, analyzing the inputted data to determine an appropriate amount of medicament to be administered to the user, and a dispenser for sizing and dispensing a therapeutically effective amount of the medicament. The medicament may be in the form of a continuous roll of oral thin film including the medicament.

48 Claims, 8 Drawing Sheets

(56) References Cited

U.S. PATENT DOCUMENTS

| | | |
|---|---|---|
| 7,484,640 B2 | 2/2009 | von Falkenhausen et al. |
| 7,591,801 B2 | 9/2009 | Brauker et al. |
| 7,792,349 B2 * | 9/2010 | Van Den Brink ............. 382/141 |
| 7,963,201 B2 * | 6/2011 | Willoughby et al. ........... 83/210 |
| 2004/0117062 A1 * | 6/2004 | Bonney et al. ................ 700/237 |
| 2004/0158349 A1 * | 8/2004 | Bonney et al. ................ 700/231 |
| 2004/0181184 A1 | 9/2004 | Ericson et al. |
| 2006/0065670 A1 * | 3/2006 | Doublet et al. .................... 221/1 |
| 2006/0163269 A1 * | 7/2006 | Anderson et al. ................ 221/72 |
| 2008/0290106 A1 * | 11/2008 | van der Klaauw et al. ....... 221/1 |
| 2008/0306434 A1 | 12/2008 | Dobbles et al. |
| 2009/0030730 A1 * | 1/2009 | Dullemen et al. ................. 705/3 |
| 2009/0049845 A1 | 2/2009 | McStravick et al. |
| 2010/0040727 A1 | 2/2010 | Myers et al. |
| 2011/0208348 A1 * | 8/2011 | Bogue ........................... 700/233 |
| 2012/0100202 A1 * | 4/2012 | Bogue ........................... 424/443 |

OTHER PUBLICATIONS

Written Opinion of the International Searching Authority for International Application No. PCT/US11/25804 dated Apr. 11, 2011.

* cited by examiner

DEVICE AND SYSTEM FOR DETERMINING, PREPARING AND ADMINISTERING THERAPEUTICALLY EFFECTIVE DOSES

FIELD OF THE INVENTION

The present invention relates to a system and method for dispensing a therapeutically effective amount of dosage containing a medicament including an instrument for inputting data from a user, analyzing the inputted data to determine an appropriate amount of medicament to be administered to the user, and a dispenser for sizing and dispensing a therapeutically effective amount of the medicament. The medicament may be in the form of a continuous roll of oral thin film including the medicament.

BACKGROUND OF THE INVENTION

Various therapeutic disorders may be treatable via administration of medicaments. However, care must often be taken to ensure that the proper amount of medicament is administered to the person in need of the treatment. Often, the amount of medicament required at a given point in time is different than the amount of medicament required at another time. For example, in some instances, the user may suffer from a severe headache or a fever, which may require a higher dosage of medicament to treat than one suffering from a mild ache. Oftentimes, the user has to select the number of pills, each having a pre-set amount of medicament, which he or she believes will alleviate the condition. Such guesswork is highly suspect and may result in the user taking too little or too much medicament for the particular instance. Thus, a system which will allow a variable amount of medicament to be dispensed to a user is desired.

Some previous systems include a medicament in a pre-determined amount, such as U.S. Pat. Nos. 6,394,306 and 7,484,640, and U.S. Publication No. 2002/0108963, which house and dispense dosages in a pre-determined and pre-sized amount. Administration of a medicament in a pre-sized and pre-determined amount may undesirably lead to inaccurate dosages of medicament. The user would need to guess the proper dosage amount (i.e., one pre-sized dosage or two), leading to potentially harmful and destructive results.

The need for a particular amount of medicament to be administered is especially true in the case of persons suffering from diabetic or other disorders wherein the body cannot create sufficient or useful insulin. In some instances, oftentimes dependent upon the particular blood sugar level of the user at any given point in time, the amount of medicament required may vary significantly. The amount of insulin required may depend upon the particular characteristics of the individual, in combination with the particular food he or she has recently eaten or plans to eat, as well as other factors. The user may inadvertently overdose (or underdose) on a given medicament, such as insulin, causing potentially severe problems.

In the case of sufferers of diabetes, such individuals may rely upon a self-monitoring blood-glucose monitor, which measures the level of glucose in the individual's blood at any given point in time. Depending on the glucose level, the individual may need to administer a particular level of insulin into his or her system. However, the particular level of insulin required is often determined by the individual, which is subject to potentially harmful error.

Further, particularly in the case of insulin, administration of insulin has traditionally been achieved via injection of a liquid form. The user may determine the amount of liquid to administer to him via injection. However, administration of a liquid form of a medicament may not always be entirely accurate, whether due to human error or due to insufficient mixing of components in the liquid solution.

Therefore, the currently exists a convenient method of determining the level of medicament required to administer a therapeutically effective dose, which avoids the problems of the prior art.

SUMMARY OF THE INVENTION

In one embodiment of the present invention, there is provided a system for dispensing an amount of film containing a medicament including: an instrument for inputting data from a user; a means for analyzing the inputted data to determine an appropriate amount of medicament to be administered to the user; an instrument for producing an output signal; a housing for storing a continuous roll of film, the film including a medicament in a known amount of medicament per unit volume of film; an instrument for receiving the output signal and assessing an amount of film needed to provide the appropriate amount of medicament to be administered to the user; and a dispenser for sizing and dispensing the amount of film.

In another embodiment of the present invention, there is provided a method of dispensing a therapeutically effective amount of a medicament-containing film, including the steps of: inputting data into a system; analyzing the data; generating an output signal based upon the analyzed data, the output signal including information related to a therapeutically effective amount of dosage; determining an amount of medicament-containing film that includes the therapeutically effective amount of medicament; and dispensing the amount of medicament-containing film.

In other embodiments of the present invention, there may be provided method of determining an amount of medicament-containing film which will provide a therapeutically effective amount of a dosage to a user, including the steps of: inputting data into a system; analyzing the data; and determining a therapeutically effective amount of a dosage based upon the analyzed data; and determining an amount of medicament-containing film that includes the therapeutically effective amount of dosage.

BRIEF DESCRIPTION OF THE FIGURES

The invention may be understood by reference to the Figures, in which.

DETAILED DESCRIPTION OF THE INVENTION

Figure 1:
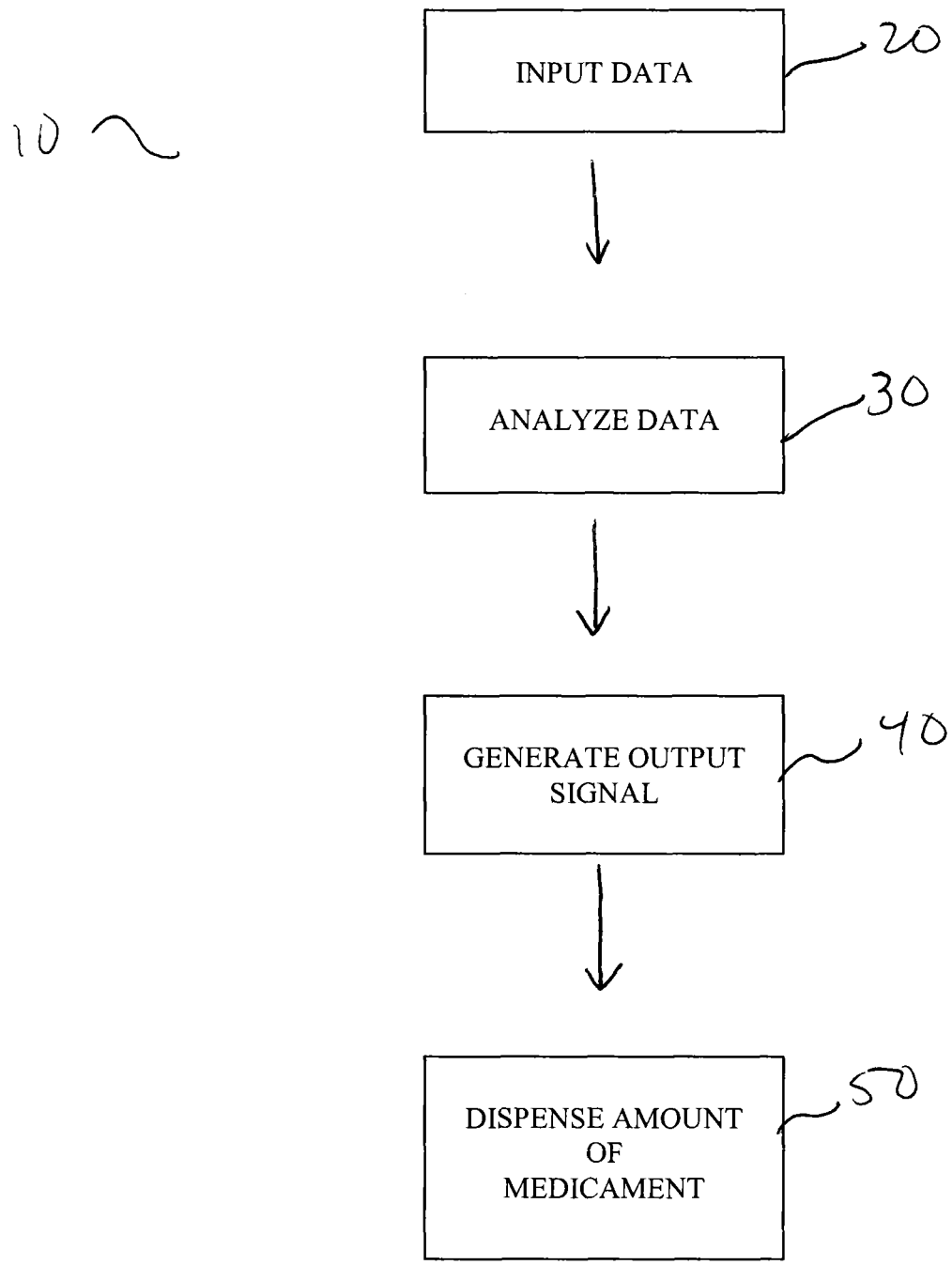
FIG. 1 is a summary of one method of determining and dispensing an amount of medicament.

As used herein, the terms "medicament", "drug" and "active agent" may be used interchangeably, and refer to a substance or composition useful for the prevention or treatment of a condition. The terms may include pharmaceuticals, neutraceuticals, cosmetic agents, biologic agents, bioeffective substances, and the like.

In some embodiments, the present invention includes the dispensing and administration of medicaments in the form of a film. It will be understood that the term "film" includes delivery systems of any thickness, including films, sheets, discs, wafers, and the like, in any shape, including rectangular, square, or other desired shape. The film may be in the form of a continuous roll of film or may be sized to a desired length. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the application of controlled drying of the film. Films may include a pouch or region of medicament between two films.

In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. In other embodiments, a topical agent is applied to a hard surface, such as a particular surface area in need of treatment.

The medicament may be dispersed throughout the film, or it may be deposited onto one or more surfaces of the film. In either way, the amount of medicament per unit length is desirably uniform throughout the film. It is desired that the films of the present invention include a uniformity of component distribution throughout the volume of a given film. Such uniformity includes a substantially uniform amount of medicament per unit length of the film, whether the medicament is within the matrix of the film or coated, laminated, or stabilized on one or more surfaces thereof. When such films are cut into individual units, the amount of the agent in the unit can be known with a great deal of accuracy. For example, for every square centimeter of film, there may be up to 40 mg of medicament. In some embodiments, there may be about 40 mg of medicament for every square centimeter of film. In the case of insulin, for example, each centimeter of film may contain up to 10 I.U. of insulin.

Uniformity of medicament throughout the film is important in administering an accurate and effective dose of medicament to a user. Various methods of forming uniform films may be used, including those described in U.S. Pat. Nos. 7,425,292 and 7,357,891 and U.S. Publication No. 2005/0037055, which are herein incorporated by reference in their entireties.

Films of the present invention may be made from any desired materials, and preferably are made from polymeric materials which are not apt to break or fracture when bent. In some embodiments, for example, the present invention includes a continuous roll of film, wherein the film is rolled. Thus, the materials selected for forming films in these embodiments are desirably flexible and strong enough to be rolled without breaking.

A wide variety of medicaments, bioactive active substances and pharmaceutical compositions may be included in the dosage forms of the present invention. Such medicaments, bioactive substances and pharmaceutical compositions may be useful as topically-administered dosages or as orally-ingestible dosages. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®), Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP®, and Aminofen®), and combinations thereof that may optionally include caffeine. Other pain relieving agents may be used in the present invention, including meperidine hydrochloride (commercially available as Demerol®), hydromorphone hydrochloride (commercially available as Dilaudid®), propoxyphene napsylate and acetaminophen (commercially available as Darvocet-N®), Fentanyl (commercially available as Duragesic® and Fentora®), sodium hyaluronate (commercially available as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium AD®), Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), and memantine (commercially available as Namenda®); anemia medication, such as cyanocobalamin (commercially available as Nascobal®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), and anastrozole (commercially available as Arimidex®); anti-coagulants, such as aspirin with extended-release dipyridamole (commercially available as Aggrenox®), warfarin sodium (commercially available as Coumadin®), dipyridamole (commercially available as Persantine®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan®), darifenacin (commercially available as Enablex®), and solifenacin succinate (commercially available as VESIcare®); blood vessel constrictors, such as methylergonovine maleate (commercially available as Methergine®); cholesterol lowering medication, including paricalcitol (commercially available as Altocor®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), wytensin. (commercially available as Guanabenz Acetate®), tenex (commercially available as Guanfacine Hydrochloride®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), Synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), and norethindrone acetate (commercially available as Aygestin); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), and paroxtine hydrochloride (available as Paxil®), aripiprazole (commercially aavialbe as Abilify®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®), and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), and topiramate (commercially available as Topamax®); treatment for shingles, such as zoster vaccine live (commercially available as Zostavax®); skin care medications, including calcipotriene (commercially available as Dovonex®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®) and eszopiclone (available as Lunesta®), zolpidem tartrate (commercially available as Ambient, Ambien CR®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/ betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysiate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is photosensitive.

Color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Moreover, fragrances can be included in the films. These may include extracts derived from plants, leaves, flowers, fruits and combinations thereof, for example.

With reference to the Figures, the present invention sets forth systems and methods for determining a therapeutically effective amount of a medicament, sizing the appropriate amount of medicament, and dispensing the appropriate amount of medicament. As used herein, the terms "therapeutically effective amount" and "appropriate amount" of medicament refer to the amount of medicament required to properly and effectively treat the condition experienced by a user at that instance. It will be understood, of course, that the "appropriate amount" of medicament may change from day to day, and even from hour to hour, depending upon the particular circumstances of that instance. The present invention is capable of determining an appropriate and therapeutically effective amount of medicament required by the user at the time in which the user practices the invention. For example, the appropriate or therapeutically effective amount of insulin may depend upon the particular blood sugar level of the user at that particular point in time. The particular dosage amount may vary significantly depending upon the particular needs and body chemistry of the user.

With reference to FIG. 1, in one aspect of the invention, a method 10 of determining and dispensing the therapeutically effective amount of medicament is provided. In this method 10, there is a first step 20 of inputting data. As will be described in further detail below, the step 20 of inputting data may include direct entry by the user of information, or it may include data generated by chemical testing of samples, such as blood or saliva.

Once the data is entered, the method 10 undergoes the next step 30 of analyzing the data. The step 30 of analyzing the data is most desirably performed by a processor, but it may be performed manually if desired. The data may be analyzed by itself or it may be analyzed in conjunction with or in comparison to other information, which may optionally be stored in the memory of the system. For example, patient information, drug information, warning information, and the like may be stored in the memory.

Once the data is analyzed, the next step 40 includes generating an output signal. The output signal may include the appropriate or therapeutically effective amount of dosage, based upon the data entered in step 20. As will be explained in more detail below, the output signal allows the system to size and dispense the therapeutically effective amount of medicament. Optionally, the system may include a display, where the user can see a depiction of the output signal. In further embodiments, the user may alter the output signal once he or she has a chance to view the depiction.

Finally, method 10 may include the step 50 of dispensing the therapeutically effective amount of medicament. As will be explained in further detail, this step 50 includes determining the appropriate dosage amount based upon the output signal. Based upon the dosage amount, the appropriate amount of medicament to dispense is determined. In embodiments wherein the medicament is in the form of a film having a substantially uniform amount of medicament per unit volume, the system described herein can provide an accurate amount of medicament by sizing the film accordingly. Once the film has been sized, it can be dispensed to a user and administered.

Figure 2:
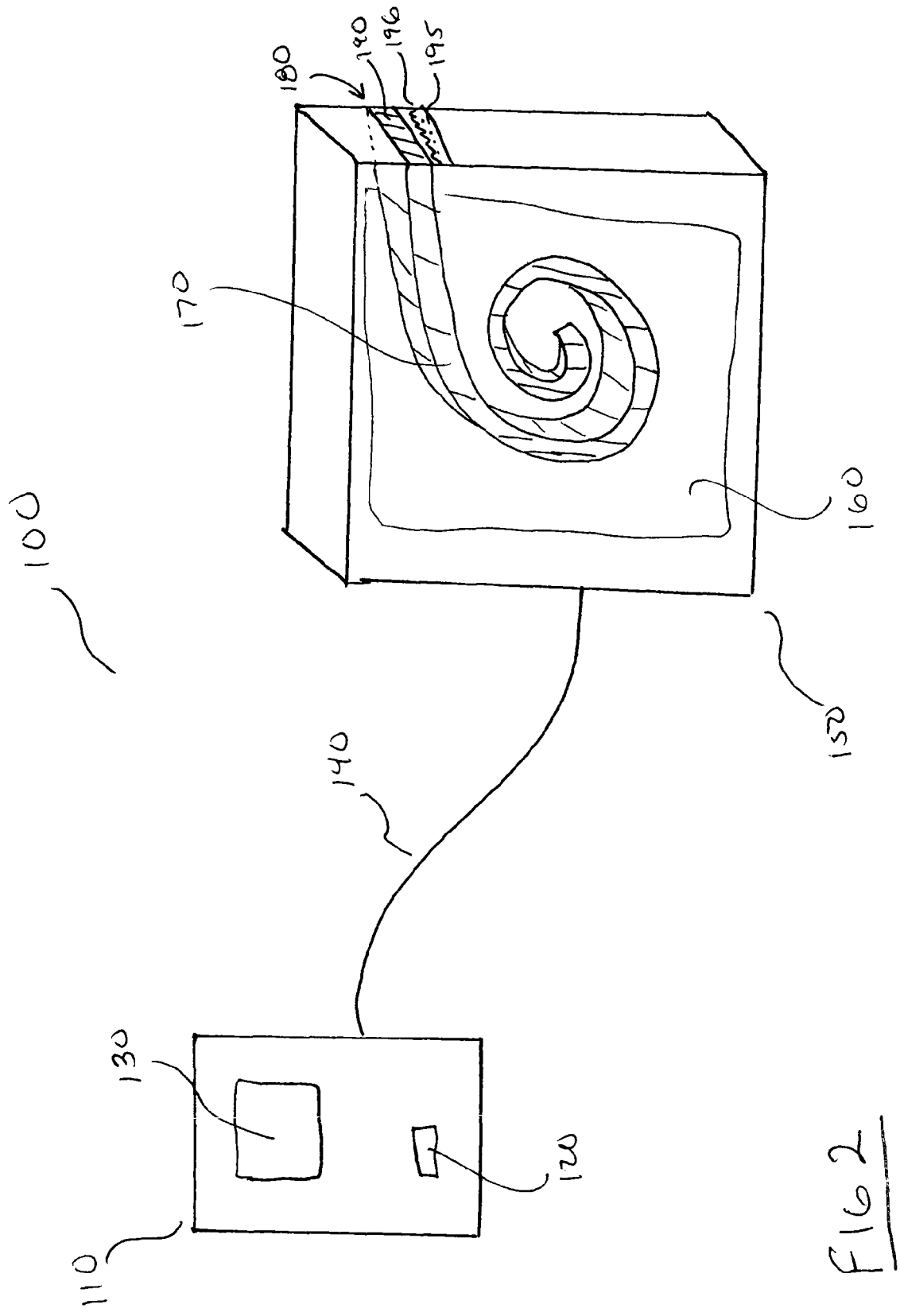
FIG. 2 is a depiction of the system of the present invention.

With respect to FIG. 2, a system 100 for analyzing data and dispensing medicament is provided. In one embodiment, the system 100 includes a processor 110. The processor 110 may be any instrument capable of processing data, and generally includes a computer. However, the processing may be completed manually, without the need for a separate processor 110. The processor 110 may be any size or shape required to process data, and may include a microprocessor. The processor 110 is in communication with an input 120. The input 120 may be housed in the same unit as the processor 110, or the input 120 and processor 110 may be housed in separate units. In embodiments where the processor 110 and input 120 are housed separately, the processor 110 and input 120 should be capable of communicating, whether via wires or wirelessly. The components of the system 100 may be powered via batteries, hard wiring, or any other available power source.

The input 120 allows the user to enter data into the system 100, thereby achieving the step 20 of inputting data. The data entered is desirably related to the user, and will be sufficient to allow the system 100 to determine the appropriate or therapeutically effective amount of medicament to be dispensed. The data may include any type of data desired, and in one embodiment the data includes data manually entered by the user, such as through a keyboard, touchpad, microphone, bar code reader, or other inputting device. For example, if the medicament is a diabetic treatment, such as insulin, the user may manually enter in a description of the food that he or she has recently eaten, or is about to eat. This information may include, for example, the caloric content of the food, as well as other characteristics, including fat content, sugar content, fiber content, and the like. Other data may include the user's height, weight, age, and combinations thereof.

The system 100 may be used to dispense pain relieving agents. In such instances, manually entered data may include a level of pain currently being experienced by the user. For example, if the medicament to be administered is an analgesic, the user may input a level of pain he or she is currently experiencing. In some embodiments, if the user is experiencing a fever and has an elevated body temperature, where the medicament is a fever-reducing agent, the user may manually input his or her body temperature.

The system 100 may be used to administer anti-anxiety agents. In such instances, the data may include the level of anxiety being experienced by the user. The system 100 may be used to administer allergy treatment medication, and the data may include the level of allergic reaction that the user is experiencing. Similarly, the system 100 may be used to administer anti-asthmatic agents, and the data may include the level of asthmatic symptoms being experienced by the user. The system 100 may be used to administer any type of medicament desired, where the data to be entered is related to the symptoms being experienced by the user at that point in time.

In some embodiments, the system 100 may require the user to input particular information as a safeguard. For example, the system 100 may require data such as the date and/or time of the last administration of medicament. This may be especially important when the medicament is one that should not be administered on multiple occasions within a given time frame. In the event that the medicament was last administered at a time that is too soon before a next dosage should properly be administered, the system 100 may refuse to provide further medicament to the user.

In some embodiments, particularly in the case of diabetic users, the input 120 may include a means for inputting chemical materials. Such materials may include, for example, blood, saliva, urine, and other bodily fluids that may be tested. The input 120 may include an instrument for accepting a chemical sample, via a strip, and determining the particular chemical characteristics of that sample. In other embodiments, the input 120 may include a finger-prick instrument, which may prick a user's finger and collect a sample of blood therefrom. Other embodiments may include using an instrument for accepting a vial or dish of the sample. The input 120 may include any means to enter a chemical sample that may be known to those of skill in the art. Chemical characteristics may include, for example, blood sugar, platelet count, blood clotting time, and combinations thereof.

In other embodiments, the input 120 may include a temperature reading apparatus, such as a thermometer. In other embodiments, the input 120 may include an apparatus into which the user may breathe, which analyzes the breath of the user. Any apparatus to sense various bodily characteristics of the user may be used as the input 120.

If desired, the system 100 may include an optional display 130. The display 130 may be a separate component, or it may be associated with one or more other components of the system 100. For example, the system 100 may include one housing that includes the processor 110, the input 120 and optional display 130. Alternatively, the housing may include simply the processor 110 and the display 130. Any display 130 may be used, and in some embodiments the display 130 includes a monitor that displays the data entered via input 120.

Once the data has been entered through the input 120, the processor 110 analyzes the data. The data may be analyzed to determine if a medicament is helpful or necessary to be administered to the user. The step 30 of analyzing the data may include any number of analyses. The processor 110 may analyze the manually entered data, or it may analyze the chemically entered data. In some embodiments, the user may input manually entered data as well as chemically entered data. In one aspect, the processor 110 will analyze only the data that has been entered, without reference to any other information or data, to determine whether and to what extent treatment is suggested or required.

In another embodiment, the processor 110 may include internal memory, which may be used to store various information related to the user. For example, the internal memory may include information regarding the user's height, weight, age, health history, and the like. The internal memory may further include information related to the administration history of the medicament. For example, the internal memory may include information related to the date and time of previous administrations of medicament, as well as the amount of medicament previously administered. In the case of diabetic users, for example, the memory may include information related to the blood sugar level of the user at previous dates and/or times, or the manually entered information regarding food that was consumed by the user.

The memory of the processor 110 may include information related to the optimal or desired characteristics of the user. For example, the memory may include information regarding the desired blood sugar level of the user. Alternatively, the memory may include information regarding the typical or optimal body temperature of the user, or other information related to the optimal body temperature of that individual.

The processor 110 may then compare the data entered through the input 120 with the data and other information stored in the internal memory, and determine the extent of treatment required. For example, the processor 110 may compare the present blood sugar level with the typical or optimal blood sugar level of the user (which is stored in the internal memory), and determine the extent of treatment required to achieve the typical or optimal blood sugar level in the user. Further, the processor 110 may analyze the caloric content of the food to be consumed by the user with the recent caloric content of food recently consumed by the user. In other embodiments, the processor 110 may compare the present body temperature of the user and compare to the typical or "optimal" body temperature, to determine the extent to which treatment is required.

Once the processor 110 has analyzed the data, a determination is made as to whether a medicament is suggested or required to be administered. In the event that a medicament may be helpful or required, the processor 110 will determine the amount of medicament that is suggested to be administered based upon the analysis of the data and/or memory. The processor 110 may then provide an output signal, which includes information directed to the amount of medicament to be administered. The output signal may then be transferred to the dispenser 150 for dispensing the medicament. In embodiments where the processor 110 and the dispenser 150 are separately housed, the output signal may be transferred via a connector 140, which may include a wire or it may be wireless. In some embodiments, the processor 110 and the dispenser 150 may be in communication via the internet or other long-distance communication means. Alternatively, the processor 110 and dispenser 150 may be housed in the same unit.

The output signal may include the amount of medicament to be administered to the user. In other embodiments, where the amount of medicament per unit volume of dosage is known, the output signal may include the amount of dosage that is to be dispensed. For example, when the dosage is in the form of a continuous roll of film, the output signal may include the amount of film to be dispensed, such as a length of film to be cut.

In embodiments incorporating an optional display 130, the display 130 may be used to display the results of the analysis. For example, the display 130 may be used to depict the amount of medicament suggested or required to be administered. The depiction may include an amount of the medicament, or alternatively it may depict the amount of dosage to be dispensed. Desirably, the display 130 will alert the user to the amount of medicament that is to be administered in a way that the user can confirm the proper amount of dosage has been dispensed. For example, the display 130 may depict the length of film to be dispensed, such that the user may compare the length of film that is actually dispensed with the length of film that is displayed, to ensure a correct dosage. If desired, the system 100 may include a further means for the user to modify the results of the analysis so as to dispense more or less medicament.

As explained above, the output signal is provided to the dispenser 150 for dispensing the medicament. The dispenser 150 may be physically connected to the processor 110, or the two may be separate. The dispenser 150 may include an optional display (not pictured). The dispenser is most desirably powered via the same power means as the processor 110, but may include a separate power means, such as batteries, hard wiring, or other power means.

In a preferred embodiment, the dispenser 150 includes a housing 160, which is used to house the medicament. The housing 160 is desirably environmentally protected, thereby ensuring safe and secure housing of the medicament. For example, the housing 160 may include a barrier to protect against moisture or debris entering, or it may include a barrier to protect against heat or light entering. In some embodiments, the housing 160 protects against the entry of moisture, light, heat and combinations thereof. Desirably, the medicament is disposed in the interior of the housing 160, protected from the outside environment. The housing 160 may optionally be kept at a particular temperature. For example, in some embodiments, medicaments are to be maintained in a cooled environment. The housing 160 may include a thermoelectric cooler or other cooling means so as to maintain a cooled environment for the medicament.

The medicament may be in any form desired. In one particularly desirable embodiment, the medicament is in the form of a film strip 170. As explained above, the film strip 170 may be made of any materials, and is desirably made of materials that are flexible and resilient, i.e., not easily broken. In some embodiments, the film strip 170 is in the form of a continuous roll of film, which is useful in conserving space in the housing 160. The film strip 170 may be an oral film, or it may be a film suitable for administration via any other desired route. The film strip 170 may be uncovered, or alternatively the film strip may have a protective layer on any side thereof. For example, the film strip 170 may include a protective layer on the surface which faces away from the center of the roll (i.e., the surface that is exposed to the interior of the housing). In some embodiments, the film strip 170 may include a protective layer on the top and bottom surfaces thereof, such as a plastic laminated covering. In still other embodiments, the film strip 170 includes a protective layer fully covering all surfaces of the film strip 170.

In one aspect of the invention, the film strip 170 is enclosed within a removable and replaceable cartridge, which may be inserted into the housing 160. The use of a removable cartridge may be particularly useful when the film strip 170 includes a pharmaceutical component. This ensures quick and easy replacement of the film strip 170 when it has been fully used, or when the expiration date has passed. This cartridge may contain machine readable information such as assay value of the drug, lot number, expiration date, total length of film and other pertinent data. For example, this machine readable information may be stored within memory housed in the cartridge, or it may contain a bar code, which is readable by the input 120.

The dispenser 150 may include a port 180, through which the film strip 170 may pass. Port 180 allows the film strip 170 to exit from the housing 160 to the outside of the dispenser 150, and ultimately to the user. It is desired that the port 180 be sized and shaped so as to snugly encompass the film strip 170, thus serving to maintain the environmental protection afforded by the housing 160. In some embodiments, the port 180 may include a cover 190, which further protects the interior of the housing 160. The cover 190 may be manually removable by the user, or it may be removably controlled by the system 100, and removable upon dispensing of the medicament.

Figure 2A:
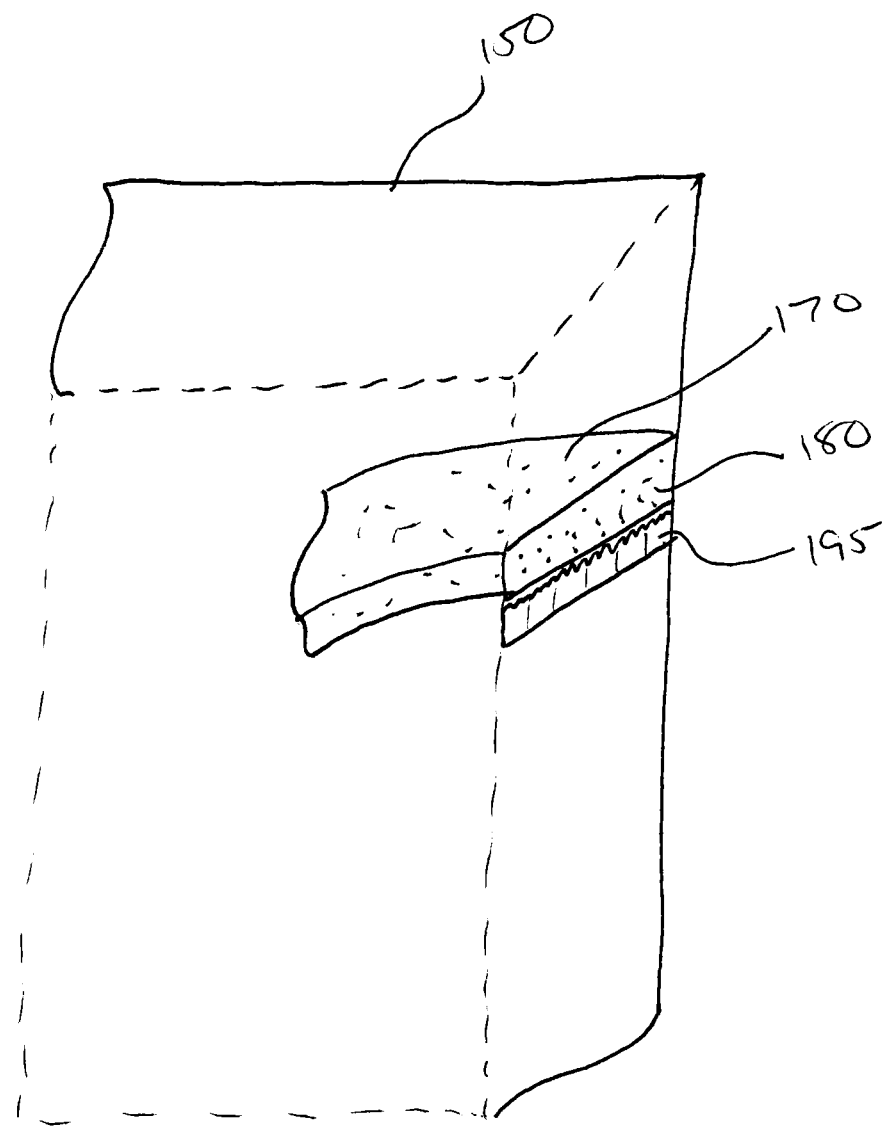
FIG. 2A is a close up view of the port and cutting means of the present invention.

In certain embodiments, particularly those where the dosage is in the form of a film strip 170, the dispenser 150 may further include a cutting means 195, which is capable of cutting the film strip 170 at a desired location. As may be seen in FIG. 2A, the cutting means 195 may be disposed at or near the port 180, and may be disposed either inside the dispenser 150 or outside the dispenser 150. The cutting means 195 may include a scissor type instrument, or it may include a saw-like instrument. The cutting means 195 may be manually operated or it may be electronically controlled by the system 100, so as to cut the film strip 170 once the proper length has been reached. Desirably, the cutting means 195 is disposed at a location near the port 180, but the cutting means 195 may be disposed at any location of the system 100, such as within the housing 160.

In one embodiment, it may be desired to include a means for sealing the film strip 170 after the cutting means 195 has cut the desired length of film strip 170. Thus, the cutting means 195 may include a sealing means 196 associated therewith. The sealing means 196 may be, for example, a heat-sealing mechanism, which may be especially useful in embodiments where the film strip 170 is housed in a laminated package. The sealing means 196 may be a mechanical sealing means, creating a seal such as a zip-type of seal or other air and moisture tight seal. The sealing means 196 may be integral to and/or associated with the cutting means 195, or it may be a separate component of the dispenser 150. Desirably, after the cutting means 195 has cut the film strip 170, the sealing means 196 effectively creates a moisture-tight and air-tight seal, protecting the remaining film strip 170 within the housing 160. In some embodiments, the cover 190 can act as a sealing means 196. For example, the cover 190 may be moved (either manually or automatically), to allow the film strip 170 to be pushed out of the dispenser 150, where it is cut to the appropriate size by the cutting means 195. The cover 190 may then be moved back to its place (again, either manually or automatically), creating a moisture- and air-tight seal for the contents of the housing 160.

Figure 3:
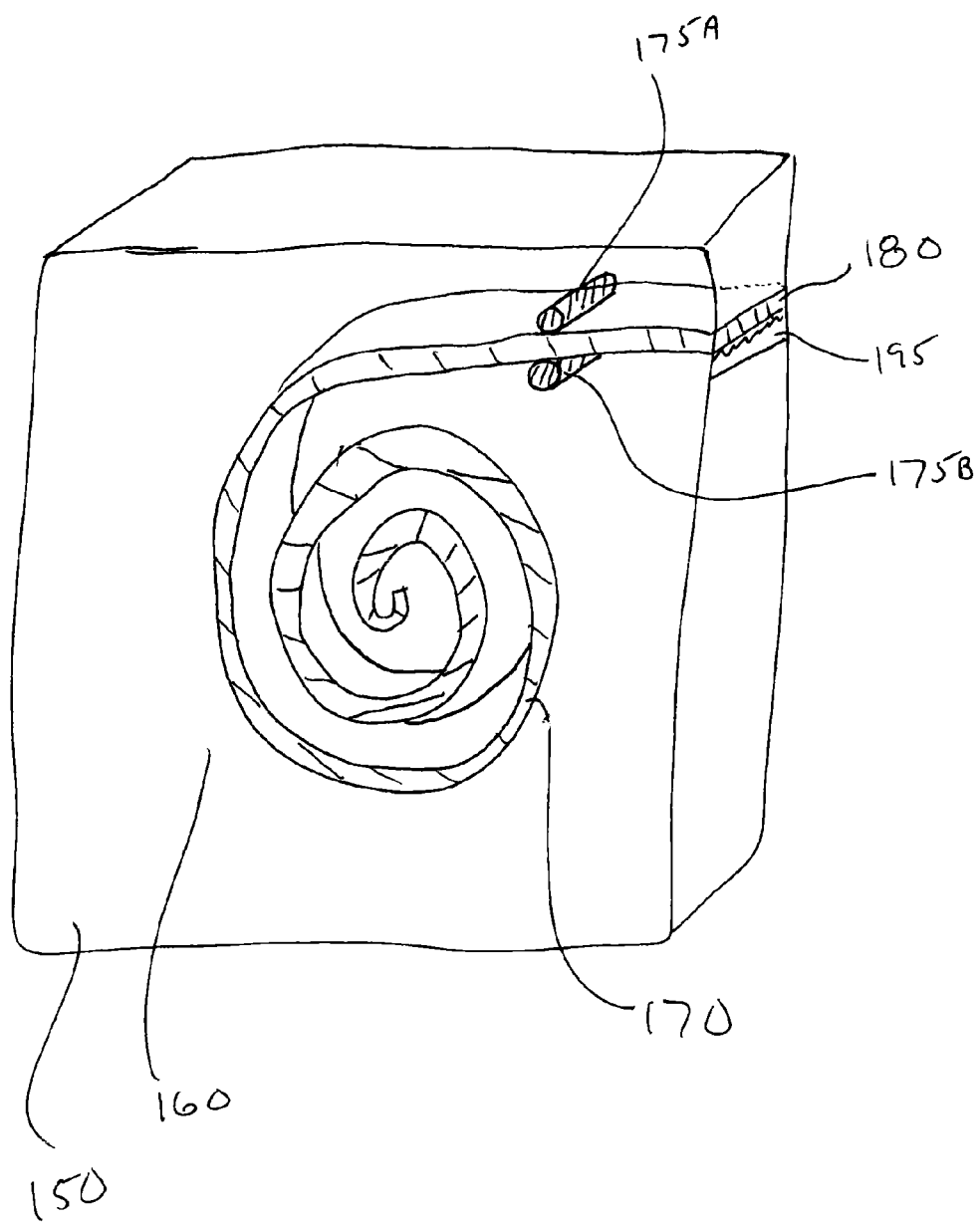
FIG. 3 is an internal view of the dispenser of the present invention.

The dispenser 150 further includes a means for forcing the film strip 170 out of the housing 160 and through the port 180. Desirably, the means for forcing the film strip 170 is accurate, such that it forces only the required length of film strip 170 out of the port 180. The means for forcing the film strip 170 may be automated or it may be manual. In one embodiment, depicted in FIG. 3, the dispenser 150 includes a roller system 175. Roller system 175 may include one roller or it may include a pair of rollers 175A, 175B, with film strip 170 disposed therebetween. Desirably, the roller system 175 is automated and controlled by the processor 110, such that the roller system 175 forces the film strip 170 to a length that the therapeutically effective amount of medicament is pushed through the port 180. Once the film strip 170 is pushed out of the housing 160 and through the port 180, the cutting means 195 may cut the film strip 170, where the user may then administer the dosage. The roller system 175 may be disposed at any location within the dispenser 150, and in one embodiment the roller system 175 is disposed at a location near the port 180 to controllably direct the film strip 170.

In this embodiment, the roller system 175 is oriented transversely with respect to the longitudinal extent of the film strip 170. Top and bottom surfaces of the film strip 170 are pressed against the roller system 175 in a fairly snug fit. The material used for the roller system 175 may include a plastic or a rubber material which creates a frictional engagement of the film strip 170 and ensures a high coefficient of static friction. The roller system 175 is desirably a smooth cylindrical body. However, the surface of the roller system 175 may alternatively be knurled or otherwise profiled. The roller system 175 may be attached to the housing 160 via an axle, drive shaft, and motor (not shown), to allow rotation of the roller(s) 175A, 175B. In a desired embodiment, the roller(s) 175A, 175B are rotated electronically so as to force the desired length of film strip 170. Alternatively, the roller system 175 may be manually moved (i.e., via a crank manually operated) so as to force the film strip 170. In some embodiments, only one roller 175A is rotated, while the other roller 175B is not rotated.

Figure 4A:
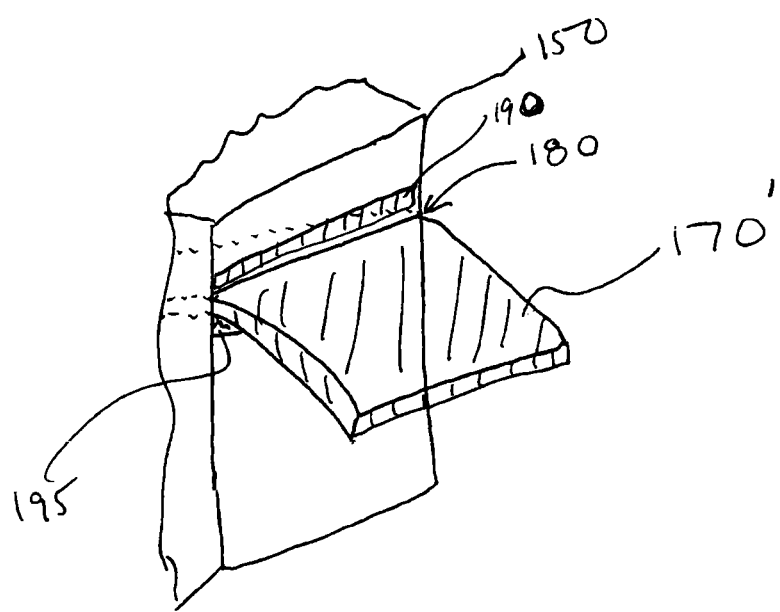
FIG. 4A is a close up of the film strip being dispensed through the dispenser.
Figure 4B:
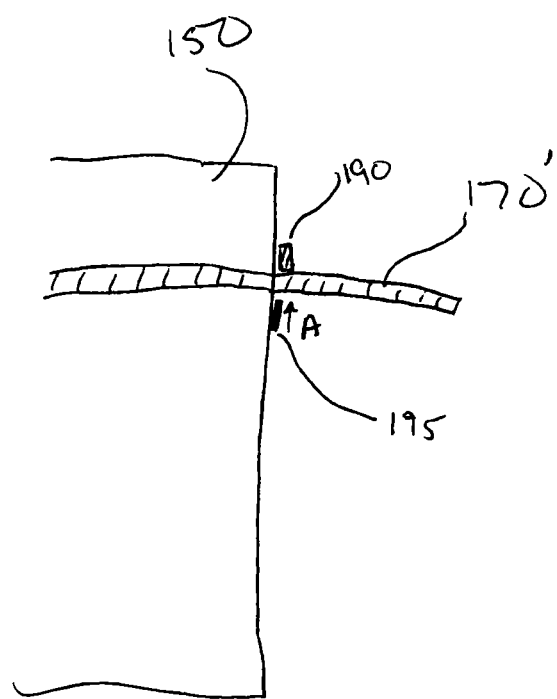
FIG. 4B is a side view of the film strip being dispensed through the dispenser.

In one embodiment, once data has been analyzed and the therapeutically effective amount of medicament has been determined, and the step 40 of generating an output signal has been performed, the step 50 of dispensing the therapeutically effective amount of medicament may be performed. As may be seen in FIGS. 4A and 4B, the therapeutically effective amount of film strip 170' is forced out of the dispenser 150 through the port 180. Once the therapeutically effective amount of film strip 170' is forced out of the dispenser 150, it may then be cut by the cutting means 195. In one embodiment, depicted in FIG. 4B, the cutting means 195 may move towards the film strip 170' in a direction A, but it is understood that any means of cutting the film strip 170 may be used, including a scissor-type of cutting, a saw-type of cutting, or laser cutting. The user may then take the cut therapeutically effective amount of film strip 170' and administer via any desired route.

In another embodiment, the cutting means 195 may be disposed within the dispenser 150, where it may cut the film strip 170 to the desired length prior to feeding the cut film strip 170' through the housing.

In embodiments where the film strip 170 has a protective cover or layer, the protective cover or layer may be cut by the cutting means 195 at the same time as the film strip 170 is cut. The user would then simply remove the protective layer or cover and expose the film strip 170 after it has been dispensed. Alternatively, the port 180 may include a means for peeling away the protective cover or layer as the film strip 170 is forced out of the port 180. One such device for peeling away a cover or layer is depicted in U.S. Pat. No. 7,484,640, the contents of which are herein incorporated by reference in their entirety. In this fashion, only the film strip 170 is ultimately forced through the port 180 and cut by the cutting means 195. The user would thus not have to subsequently peel away the cover or layer after the film strip 170 is cut.

Figure 5:
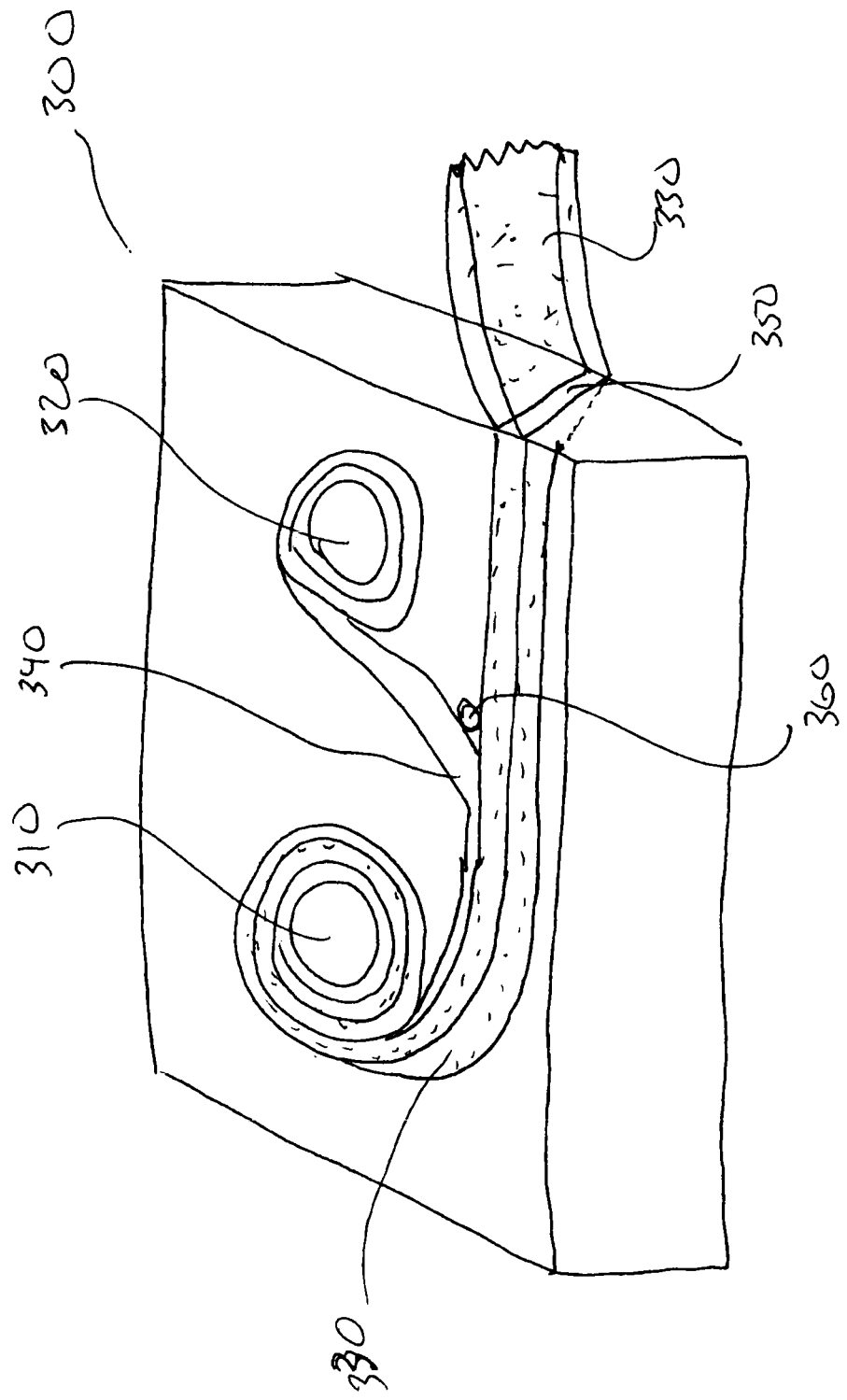
FIG. 5, depicts a dual-reel cassette which may be used in the present invention.

In another embodiment, depicted in FIG. 5, the system may include a removable double reel cassette 300 having a first reel 310 and second reel 320. The film 330, including an optional protective backing layer 340, may be wound on the first reel 310. The film 330 is directed from the cassette 300 through an opening 350, where it may be dispensed to the user. In this embodiment, as the film 330 is dispensed from the cassette 300, the protective backing layer 340 may be peeled away via peeling member 360, and wound onto the second reel 320. Only the film 330 (which has been separated from the protective backing layer 340) is dispensed to the user. Once the entire roll of film 330 has been dispensed, the second reel 320 and protective backing layer 340 may be discarded. This allows easy cleanup and safe removal of waste materials.

Figure 6:
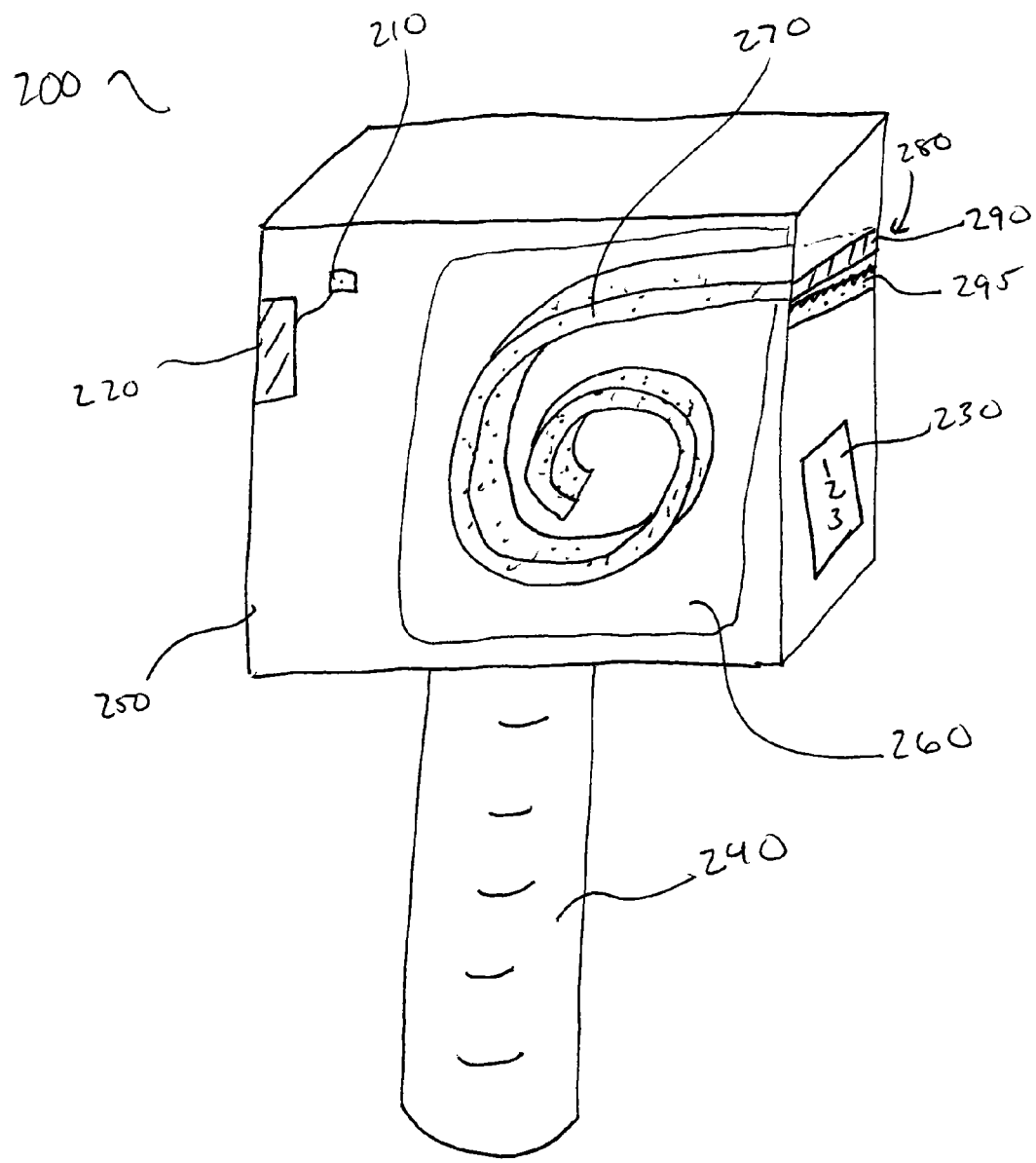
FIG. 6 is a depiction of one embodiment of the system of the present invention which is hand-held.

In another embodiment of the present invention, set forth in FIG. 6, system 200 may include a unitary, hand-held instrument. In this embodiment, the system 200 includes a processor 210, input 220, and dispenser 250 housed in one instrument. Optionally, the system 200 may include a handle 240, such that the user may hold the system 200. The dispenser 250 may further include a housing 260, film strip 270, port 280, optional cover 290, optional cutting means 295 and optional sealing means 296, as described above. Optionally, the system 200 may include a display means 230, as described above.

In another embodiment, similar to that described in FIG. 6, the system 200 may include a unitary, hand-held instrument that is pocket sized. As used herein, the term "pocket sized" is intended to include any size that may comfortably be contained in the user's pocket, and generally includes systems between about 5 to about 15 centimeters in length and about 4 to about 10 centimeters in width.

The present invention further provides a kit for analyzing data and dispensing a therapeutically effective amount of a medicament. In this embodiment, the kit includes processor 110, input 120 and dispenser 150, each as described above. Each component may be separate instruments or they may be combined together in one instrument.

Thus, in a preferred method 10 of dispensing a medicament, system 100 is first provided. The user then enters data through input 120 (step 20), which is analyzed by processor 110 (step 30). The data may be depicted on an optional display 130. The data may be analyzed by itself or it may be analyzed in conjunction with and/or in comparison to other data that has been stored in an optional memory. The processor 110 analyzes the data and determines an appropriate or therapeutically effective amount of medicament to be administered to the user. This amount may be depicted on the optional display 130, if desired. An output signal is generated (step 40), which includes the amount of medicament to be administered to the user. The output signal is communicated to the dispenser 150, for example, via connector 140.

The dispenser 150 may then dispense the appropriate or therapeutically effective amount of medicament to the user. In a preferred embodiment, the medicament is in the form of a continuous roll of film 170, which is contained in housing 160. In this embodiment, the film 170 contains a known amount of medicament per unit volume. As such, a length of film 170 which corresponds to the amount of medicament may be dispensed to the user. The dispenser 150 would then measure an appropriate length of film 170, and direct this particular amount of film 170 to the user via port 180. In one embodiment, once the appropriate or therapeutically effective amount of medicament is directed out of the port, the cutting means 195 may be used to cut the film 170, thereby providing an accurate dosage to the user.

In some embodiments, the present invention sets forth a method of determining the proper length of a film strip 170 containing a known amount of medicament per unit volume. In this method, a system 100 may be provided which includes a processor 110 and input 120. The user may provide data via input 120 as described above (the data may be manually entered, provided via a sample, or combinations thereof). The processor 110 then analyzes the data as set forth above, either analyzing the data itself or the data in conjunction with any stored information in internal memory. The processor 110 thus determines whether administration of medicament is suggested or required, and the amount of medicament to be administered. This amount may be displayed on an optional display 130.

The internal memory may include information related to the known amount of medicament per unit volume of film 170. The processor 110 may perform a simple calculation including the desired amount of medicament and the known amount of medicament per unit volume to determine the appropriate volume of film 170 to be administered. Desirably, the amount of film 170 to be administered is depicted on the optional display 130, so that the user is capable of seeing the desired amount of film 170 to be administered. The user may then acquire that amount of film 170 manually, or the user may enter it into a dispenser 150.

It should be understood that various alternatives to the embodiments of the present invention described herein can be employed in practicing the present invention. While particular embodiments of the present invention have been described herein for purposes of illustration, many modifications and changes will become apparent to those skilled in the art. Accordingly, the claims set forth herein are intended to encompass all such modifications and changes as fall within the true spirit and scope of this invention.

What is claimed is:

1. A system for dispensing an amount of film containing a medicament comprising:
   a. an instrument for inputting contemporaneously produced user related data from a user;
   b. a processor for analyzing said inputted contemporaneously produced user related data to determine an appropriate and therapeutically effective amount of medicament required by the user at the time at which the user uses the system;
   c. an instrument for producing an output signal;
   d. a housing for storing a continuous roll of film, said film comprising a medicament in a known amount of medicament per unit volume of film;
   e. an instrument for receiving said output signal and determining an amount of film which includes said appropriate amount of medicament to be administered to said user; and
   f. a dispenser for sizing and dispensing said amount of film.

2. The system of claim 1, wherein said data comprises manually entered data.

3. The system of claim 1, wherein said data comprises chemical data.

4. The system of claim 3, wherein said chemical data comprises a bodily fluid.

5. The system of claim 4, wherein said bodily fluid comprises saliva, blood, urine, mucous material, tears, perspiration, and combinations thereof.

6. The system of claim 4, wherein said instrument for inputting data from a user comprises a means for accepting said bodily fluid.

7. The system of claim 1, wherein said data comprises information selected from the group consisting of information related to food consumed by said user, information related to food to be consumed by said user, information related to the level of pain experienced by said user, information related to the body temperature of said user, information related to the level of allergic reaction experienced by the user, blood clotting time, prothrombin time, platelet count, and combinations thereof.

8. The system of claim 1, wherein said processor comprises internal memory.

9. The system of claim 8, wherein said memory includes stored data.

10. The system of claim 9, wherein said stored data comprises information related to said user.

11. The system of claim 10, wherein said information related to said user comprises information selected from the group consisting of the user's age, the user's height, the user's weight, user's sex, user's ethnic origin, users medical history, the typical body temperature of the user, the last time medicament was administered to said user, the amount of medicament last administered to said user, maximum allowable dosage of medicament, historical data of medicament administration for the duration of the film cartridge and combinations thereof.

12. The system of claim 9, wherein said processor analyzes said inputted data and said stored data to determine an appropriate amount of medicament to be administered to said user.

13. The system of claim 1, wherein said appropriate amount of medicament to be administered to said user is the amount of medicament necessary to treat a condition experienced by said user.

14. The system of claim 13, wherein said condition comprises pain.

15. The system of claim 13, wherein said condition comprises fever.

16. The system of claim 13, wherein said condition comprises a blood sugar level.

17. The system of claim 13, wherein said condition comprises an insulin level.

18. The system of claim 13, wherein said condition comprises a platelet level.

19. The system of claim 13, wherein said condition comprises a blood clotting time.

20. The system of claim 13, wherein said condition comprises a prothrombin time.

21. The system of claim 1, wherein said output signal comprises the appropriate amount of medicament to be administered to said user.

22. The system of claim 21, wherein said instrument for producing an output signal comprises a display.

23. The system of claim 22, wherein said display conveys the appropriate amount of medicament to be administered to said user.

24. The system of claim 1, wherein said continuous roll of film has a protective layer.

25. The system of claim 1, wherein said housing is moisture-impermeable.

26. The system of claim 1, wherein said housing is heat-impermeable.

27. The system of claim 1, wherein said housing is light-impermeable.

28. The system of claim 1, wherein said housing is maintained at a desired temperature.

29. The system of claim 28, wherein said housing comprises a cooler.

30. The system of claim 1, wherein said amount of film needed to provide the appropriate amount of medicament to be administered to said user comprises a volume of film.

31. The system of claim 30, wherein said instrument for receiving said output signal determines the length of film to provide said volume of oral thin film.

32. The system of claim 1, wherein said dispenser is in communication with said housing, such that said amount of film may be dispensed from said housing through said dispenser.

33. The system of claim 32, wherein said dispenser comprises a port, which is sized to allow said film to pass therethrough.

34. The system of claim 33, wherein said port comprises a removable cover.

35. The system of claim 34, wherein said removable cover is automatically moved when said film is being dispensed.

36. The system of claim 34, wherein said removable cover may manually be removed to dispense said film.

37. The system of claim 33, wherein said dispenser comprises a cutting means.

38. The system of claim 37, wherein said cutting means is used to cut said film to the appropriate length so as to provide the amount of medicament needed.

39. The system of claim 1, wherein said medicament comprises a biologic.

40. The system of claim 1, wherein said medicament comprises insulin.

41. The system of claim 1, wherein said medicament comprises an analgesic.

42. The system of claim 1, wherein said medicament comprises a blood clotting agent.

43. The system of claim 1, wherein said instrument for inputting data and said housing are connected via a wire.

44. The system of claim 1, wherein said instrument for inputting data and said housing are housed in one unit.

45. The system of claim 44, wherein said housing is handheld.

46. The system of claim 45, wherein said housing is pocket sized.

47. The system of claim 1, wherein said roll of film is housed in a cartridge.

48. The system of claim 47, wherein said cartridge is replaceable in said housing.

* * * * *